US011028384B2

(12) United States Patent
Kortmann et al.

(10) Patent No.: US 11,028,384 B2
(45) Date of Patent: Jun. 8, 2021

(54) PYRUVATE CARBOXYLASE AND PYRUVATE CARBOXYLASE-ENCODING DNA, PLASMID CONTAINING SAID DNA AND MICROORGANISM FOR THE PRODUCTION THEREOF, AND METHODS FOR THE PRODUCTION OF PRODUCTS THE BIOSYNTHESIS OF WHICH INCLUDES OXALOACETATE AS PRECURSOR, AND CHROMOSOME

(71) Applicant: FORSCHUNGSZENTRUM JUELICH GMBH, Juelich (DE)

(72) Inventors: Maike Kortmann, Aachen (DE); Meike Baumgart, Pulheim (DE); Michael Bott, Juelich (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 16/606,230

(22) PCT Filed: Apr. 13, 2018

(86) PCT No.: PCT/DE2018/000104
§ 371 (c)(1),
(2) Date: Oct. 18, 2019

(87) PCT Pub. No.: WO2018/210358
PCT Pub. Date: Nov. 22, 2018

(65) Prior Publication Data
US 2020/0056166 A1 Feb. 20, 2020

(30) Foreign Application Priority Data

May 18, 2017 (DE) .................... 10 2017 004 751.0

(51) Int. Cl.
C12N 15/63 (2006.01)
C12N 9/00 (2006.01)
C12N 15/52 (2006.01)
C12N 15/74 (2006.01)
C12P 21/00 (2006.01)

(52) U.S. Cl.
CPC ............. *C12N 9/93* (2013.01); *C12N 15/52* (2013.01); *C12N 15/74* (2013.01); *C12P 21/00* (2013.01); *C12Y 604/01001* (2013.01)

(58) Field of Classification Search
CPC ................... C12Y 604/01001; C12N 15/63
See application file for complete search history.

(56) References Cited

U.S. PATENT DOCUMENTS 4,346,170 A 8/1982 Sano et al.
5,827,698 A 10/1998 Kikuchi et al.
6,884,606 B2 4/2005 Sinskey et al.
7,300,777 B2 11/2007 Guillouet et al.
2008/0014618 A1 1/2008 Bathe et al.
2015/0284760 A1 10/2015 Binder et al.

FOREIGN PATENT DOCUMENTS

| DE | 19831609 A1 | 4/1999 |
| DE | 102012016716 A1 | 2/2014 |
| EP | 1067193 A1 | 1/2001 |
| EP | 2194122 B1 | 12/2015 |
| JP | S5618596 A | 2/1981 |
| JP | S 5618596 A | 2/1981 |
| WO | WO 9617930 A1 | 6/1996 |
| WO | WO 2008006680 A2 | 1/2008 |

OTHER PUBLICATIONS

Maike Kortmann, et al., "Pyruvate Carboxylase Variants Enabling Improved Lysine Production from Glucose Identified by Biosensor-Based High-Throughput Fluorescence-Activated Cell Sorting Screening", ACS Synthetic Biology, vol. 8, Dec. 2019, pp. 274-281.
Julia Frunzke, et al., "Co-ordinated regulation of gluconate catabolism and glucose uptake in Corynebacterium glutamicum by two functionailly equivalent transcriptional regulators, GntR1 and GntR2", Molecular Microbiology, vol. 67, No. 2, Nov. 6, 2007, 305-322.
Petra G., et al., "Pyruvate Carboxylase is a Major Bottleneck for Glutamate and Lysine Production by Corynebacterium glutamicum", J. Mol. Microbiol. Biotechnol., vol. 3, No. 2, Oct. 16, 2000, pp. 295-300.
Guo, et al., "Enhancing the Supply of Oxaloacetate for L-Glutamate Production by pyc Overexpression in Different Corynebacterium glutamicum," *Biotechnol Lett* 35: 943-950 (May 21, 2013).
Neuner, et al., "Mixed Glucose and Lactate Uptake by Corynebacterium glutamicum Through Metabolic Engineering," *Biotechnol J* 6: 318-329 (Feb. 9, 2011).
Neuner, et al., "Production of L-lysine on Different Silage Juices Using Genetically Engineering Corynebacterium glutamicum," *J of Biotechnology* 163: 217-224 (Aug. 9, 2012).
Blombach, et al., "Effect of Pyruvate Dehydrogenase Complex Deficiency on L-lysine Production with Corynebacterium glutamicum," *Appl Microbiol Biotechnol* 76: 615-623 (Mar. 2, 2007).
Shirai, et al., "Study on Rules of Anaplerotic Pathways in Glutamate Overproduction of Corynebacterium glutamicum by Metabolic Flux Analysis," *Microbial Cell Factories* 6, 19: 1-11 (Jun. 23, 2007).
Riedel, et al., "Characterization of the Phosphoenolpyruvate Carboxykinase Gene from Corynebacterium glutamicum and Significance of the Enzyme for Growth and Amino Acid Procduction," *J Mol Microbiol Biotechnol* 3, 4: 573-583 (Dec. 2001).
Hoefel, et al., "Comparative Reaction Engineering Studies for Succinic Acid Production from Sucrose by Metabolically Engineered *Escherichia coli* in Fed-Batch-Operated Stirred Tank Bioreactors," *Biotechnol J* 7: 1277-1287 (May 16, 2012).
Meng, et al., "High-Yield Anaerobic Succinate Production by Strategically Regulating Multiple Metabolic Pathways Based on Stoichiometric Maximum in *Escherichia coli,*" *Microbial Cell Factories* 15, 141: 1-13 (Dec. 2016).

(Continued)

Primary Examiner — Tekchand Saidha
(74) *Attorney, Agent, or Firm* — Leydig, Voit & Mayer, Ltd.

(57) ABSTRACT

A DNA sequence that includes at least 70% identity with respect to SEQ ID NO: 1 and further includes a triplet at position 1027-1029 that codes for alanine.

25 Claims, 4 Drawing Sheets

Specification includes a Sequence Listing.

(56) References Cited

OTHER PUBLICATIONS

Litsanov, et al., "Toward Homosuccinate Fermentation: Metabolic Engineering of Corynebacterium glutamicum for Anaerobic Production of Succinate from Glucose and Formate," *Applied and Environmental Microbiology* 78, 9: 3325-3337 (Mar. 2, 2012).

Tajima, et al., "Effects of Eliminating Pyruvate Node Pathways and of Coexpression of Heterogeneous Carboxylation Enzymes on Succinate Production by Enterobacter aerogenes," *Applied and Environmental Microbiology* 81, 3: 929-937 (Nov. 21, 2014).

Li, et al., "Enhanced Succinate Production from Glycerol by Engineered *Escherichia coli* strains," *Bioresource Technology* 218: 217-223 (Jun. 25, 2016).

Okino, et al., "An Efficient Succinic Acid Production Process in a Metabolically Engineered Corynebacterium glutamicum Strain," *Applied Microbiology Biotechnology* 81: 459-464 (Sep. 6, 2008).

Nguyen, et al., "Fermentative Production of the Diamine Putrescine: System Metabolic Engineering of Corynebacterium Glutamicum," *Metabolites* 5: 211-231 (Apr. 24, 2015).

Ohnishi, et al., "A Novel Methodology Employing Corynebacterium glutamicum Genome Information to Generate a New L-lysine-producing Mutant," *Appl Microbiol Biotechnol* 58: 217-223 (Dec. 8, 2001).

Kind, et al., "Systems-Wide Metabolic Pathway Engineering in Corynebacterium glutamicum for Bio-Based Production of Diaminopentane," *Metabolic Engineering* 12: 341-351 (Apr. 8, 2010).

Deng, et al., "Metabolic Engineering of a Laboratory-Evolved Thermobifida Fusca muC Strain for Malic Acid Production on Cellulose and Minimal Treated Lignocellulosic Biomass," *Biotechnol Prog* 32, 1: 14-20 (Jan. 23, 2016).

Hochheim, et al., "Mutations in MurE, the Essential UDP-N-acetylmuramoylalanyl-D-glutamate 2,6-diaminopimelate ligase of Corynebacterium glutamicum: Effect on L-lysine Formation and Analysis of Systemic Consequences," *Biotechnol Lett* 39: 283-288 (Oct. 25, 2016).

Schaefer, et al., "Small Mobilizable Multi-Purpose Cloning Vectors Derived from the *Escherichia coli* plasmids pK18 and pK19: Selection of Defined Deletions in the Chromosome of Corynebacterium glutamicum," *Gene* 145: 69-73 (Mar. 14, 2994).

PYRUVATE CARBOXYLASE AND PYRUVATE CARBOXYLASE-ENCODING DNA, PLASMID CONTAINING SAID DNA AND MICROORGANISM FOR THE PRODUCTION THEREOF, AND METHODS FOR THE PRODUCTION OF PRODUCTS THE BIOSYNTHESIS OF WHICH INCLUDES OXALOACETATE AS PRECURSOR, AND CHROMOSOME

CROSS REFERENCE TO RELATED APPLICATIONS

This application is a U.S. National Phase Application under 35 U.S.C. § 371 of International Application No. PCT/DE2018/000104, filed on Apr. 13, 2018, and claims benefit to German Patent Application No. DE 10 2017 004 751.0, filed on May 18, 2017. The International Application was published in German on Nov. 22, 2018 as WO 2018/210358 under PCT Article 21(2).

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 53,101 bytes ASCII (Text) file named "817249_ST25.txt," created Oct. 10, 2019.

FIELD

The invention relates to a pyruvate carboxylase and a DNA encoding for pyruvate carboxylase, to a plasmid containing the DNA, and to a microorganism for production, and to a method for the production of products whose biosynthesis includes oxaloacetate as precursor, and to a chromosome.

BACKGROUND

*Corynebacterium glutamicum* is used industrially for the preparation of amino acids, in particular L-glutamate and L-lysine. For the production of L-lysine, the intermediate oxaloacetate is withdrawn from the citrate cycle since it serves as a precursor for amino acids or salts of the amino acids of the aspartate family. These are L-aspartate, L-asparagine, L-lysine, L-methionine, L-threonine and L-isoleucine. In order that the citrate cycle can continue to run despite the withdrawal of these intermediates, it must be replenished by what are known as anaplerotic reactions. When grown on sugars, the oxaloacetate pool is replenished by the carboxylation of pyruvate or phosphoenolpyruvate to oxaloacetate. The ATP-dependent formation of oxaloacetate from pyruvate and carbon dioxide or $HCO_3^-$ is catalyzed by the enzyme pyruvate carboxylase (Pyc). Accordingly, a high Pyc activity is important for the industrial microbial production of amino acids of the aspartate family, such as L-lysine, for example, and of the glutamate family, such as L-glutamate, for example. High Pyc activity is also beneficial for the production of other metabolites that derive from intermediates of the citrate cycle.

The enzymatic activity of the native Pyc of *C. glutamicum* is inhibited allosterically, inter alia, by aspartate, and therefore has only limited activity at high intracellular aspartate concentrations. Thus, the production of L-lysine and other oxaloacetate-derived products is also limited, since only a limited amount of the precursor metabolites is provided. The Pyc variants described thus far only lead to a moderate increase in L-lysine production.

The publication by Peters-Wendisch et al., "Pyruvate carboxylase is a major bottleneck for glutamate and lysine production by *Corynebacterium glutamicum*" in the Journal of Molecular Microbiology and Biotechnology (2001) 32: 295-300, discloses that the deletion of the pyc gene in the *C. glutamicum* DG52-5 strain results in a 60% reduction in the lysine titer, whereas plasmid-mediated overexpression of the pyc gene in the G52-5 strain results in a lysine titer increased by 50%. Furthermore, the deletion of the pyc gene in the wild-type strain ATCC13032 is shown to reduce the L-glutamate production induced by Tween 60 by approximately 50%, whereas plasmid-based overexpression of the pyc gene increases glutamate formation by 700%. The importance of a high Pyc activity for the production of lysine and glutamate was also demonstrated subsequently in other publications (Blombach et al., 2007 Applied Microbiology and Biotechnology 76: 615-623; Shirai et al., 2007 Microbial Cell Factories 6: 19; Neuner and Heinzle, 2011 Biotechnology Journal 6: 318-329; Neuner et al., 2013 Journal of Biotechnology 163: 217-224; Guo et al. 2013 Biotechnology Letters 35: 943-950).

A high Pyc activity is also of particular importance for the production of other metabolites, with the exception of amino acids which constitute intermediates of the citrate cycle or are derived from intermediates of the citrate cycle. The publications by Shoea Okino et al., "An efficient succinic acid production process in a metabolically engineered *Corynebacterium glutamicum* strain" in Appl. Microbiol. Biotechnol. (2008) 81: 459-464, and Torben Hoefel et al., "Comparative reaction engineering studies for succinic acid production from sucrose by metabolically engineered *Escherichia coli* in fed-batch-operated stirred tank bioreactors" in Biotechnol. J. 2012, 7, 1277-1287, disclose that the expression or overexpression of genes encoding for a pyruvate carboxylase results in a production or increased production of succinate. This is also demonstrated in further publications (Li et al., 2016 Bioresource Technology 218: 217-223; Tajima et al., 2015 Applied and Environmental Microbiology 81: 929-937; Litsanov et al., 2012 Applied and Environmental Microbiology 78: 3325-3337; Meng et al., 2016 Microbial Cell Factories 15: 141). Increased Pyc activity has also proven beneficial for the production of malate with *Thermobifida fusca* (Deng et al., 2016 Biotechnology Progress 31: 14-20). An amplification of the Pyc activity has also been used for the production of diamines derived from citrate cycle intermediates, such as, for example, putrescine (1,4-diaminobutane) or cadaverine (1,5-diaminopentane) (Nguyen et al., 2015 Metabolites 5: 211-231; Kind et al., 2010 Metabolic Engineering 12: 341-351).

Ohnishi et al., (Applied Microbiology and Biotechnology (2002) 58: 217-223) described the chromosomal introduction of the proline to serine amino acid exchange at position 458 of the Pyc of *C. glutamicum* in the *C. glutamicum* strain AHD2, which is based on the wild-type ATCC 13032 and carries two point mutations, Val59Ala in the gene for the homoserine dehydrogenase (hom) and Thr311Ile in the gene for aspartate kinase (lysC). The AHP-3 strain with the pyc P458S mutation formed 6% more L-lysine than the parental strain AHD-2. The authors describe that there is no known selectable phenotype for the identification of the pyc mutation, and it is presumably to be found only by comparative genome analysis. In addition, the Pyc variant Pyc P458S has not yet been characterized any further.

The document U.S. Pat. No. 7,300,777 B2 describes an organism in which a pyruvate carboxylase from the *C. glutamicum* strain NRRL-B11474 having multiple mutations (M1V, E153D, A182S, A206S, H227R, A452G, D1120E) was isolated with respect to the Pyc from the *C. glutamicum* strain ATCC 21523. At least one of the said mutations results in a Pyc variant which is stimulated up to 2.5 times in its activity by aspartate in low concentrations (1-10 mM) and is inhibited again at higher aspartate concentrations, up to a maximum of 30% of the activity in the absence of aspartate. At 30 mM aspartate, the Pyc from the NRRL-B11474 strain still exhibited the same activity as in the absence of aspartate, whereas at 30 mM aspartate the Pyc of the ATCC 21523 strain had only 30% of the activity it exhibited in the absence of aspartate. However, the effect of the feedback-resistant Pyc variant from *C. glutamicum* NRRL-B11474 on the fermentative production of amino acids, in particular L-lysine and L-glutamate, was not disclosed in the document U.S. Pat. No. 7,300,777 B2.

German patent application 102012016716.4 discloses a screening method by means of which improved enzymes can be discovered.

SUMMARY

In an embodiment, the present invention provides a DNA sequence. The DNA sequence includes at least 70% identity with respect to SEQ ID NO: 1. A triplet at position 1027-1029 codes for alanine.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
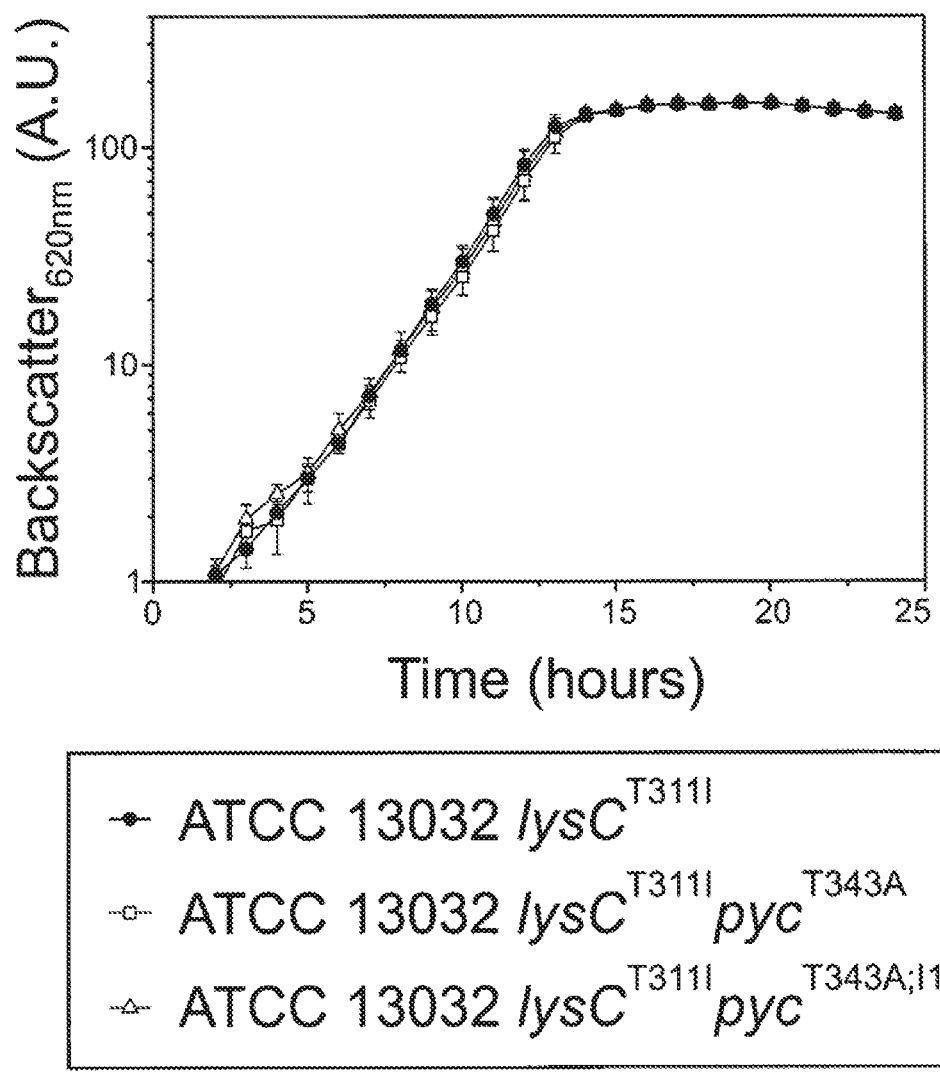
FIG. 1 illustrates growth of *C. glutamicum* ATCC 13032 lysC$^{T311I}$ with native Pyc, chromosomally encoded Pyc$^{T343A}$, and chromosomally encoded Pyc$^{T343A;I1012S}$.

The invention provides a microorganism, a pyruvate carboxylase, an encoding gene for the pyruvate carboxylase, a plasmid or chromosome containing said gene, and a method for production of products whose biosynthesis includes oxaloacetate as a precursor, by means of which the yield, titer, volumetric productivity (g product/liter/hour), or the specific productivity (g product/hour/g of cell dry mass) can be increased in the production of products derived from oxaloacetate. In particular, the production of amino acids of the aspartate family, that is to say L-lysine, L-aspartate, L-asparagine, L-threonine, L-isoleucine, and L-methionine, can be increased. Furthermore, the production of amino acids of the glutamate family, such as L-glutamate, L-glutamine, L-arginine, or L-proline; of intermediates, such as salts and acids of the citrate cycle, for example succinate, malate, fumarate, 2-oxoglutarate, citrate, or isocitrate; of diamines, such as, for example, 1,5-diaminopentane or 1,4-diaminobutane; or also of further products, such as itaconate, ectoine, gamma aminobutyrate, butanol, 1-propanol, L-citrulline, L-ornithine, D-arginine, or 4-hydroxyproline, can be increased.

With the microorganism, the pyruvate carboxylase, the gene encoding for the pyruvate carboxylase, the plasmid or chromosome containing said gene, and with the preparation method, the yield of products whose biosynthesis includes oxaloacetate as a precursor can be increased. In particular, the production of amino acids of the oxaloacetate/aspartate family, that is to say L-lysine, L-aspartate, L-asparagine, L-threonine, L-isoleucine, L-methionine, can be increased. Furthermore, the production of amino acids of the glutamate family, such as L-glutamate, L-glutamine, L-arginine, or L-proline; of intermediates such as salts and acids of the citrate cycle, for example succinate, malate, fumarate or 2-oxoglutarate, citrate or isocitrate; of diamines, for example 1,5-diaminopentane or 1,4-diaminobutane; or also of further products, such as itaconate, ectoine, gamma-aminobutyrate, butanol, 1-propanol, L-citrulline, L-ornithine, D arginine, or 4-hydroxyproline, can be increased.

In the following, the invention is described in its general form, without this being interpreted restrictively.

Surprisingly, it was found that a pyruvate carboxylase modified with respect to the *C. glutamicum* ATCC 13032 lysC$^{T311I}$ strain, exchanging threonine in position 343 for alanine, and a genetically modified encoding gene for said pyruvate carboxylase, a plasmid containing said gene, and a microorganism containing said gene or plasmid, as well as the production method, can achieve increased production of products derived from oxaloacetate. For example, a final concentration of L-lysine increased by 15% with respect to the ATCC 13032 lysC$^{T311I}$ strain can be determined for the production of L-lysine.

In a preferred variant, in addition to exchanging threonine in position 343 for alanine, a pyruvate carboxylase modified with respect to the *C. glutamicum* ATCC 13032 lysC$^{T311I}$ strain additionally comprises an exchange of isoleucine in position 1012 for serine. Accordingly, the invention also relates to a genetically modified encoding gene for said pyruvate carboxylase having the modifications T343A and I1012S; to a plasmid containing said gene; and to a microorganism containing said gene or plasmid; and to the production method. In this embodiment, a final concentration of L-lysine that is increased by 9 to 19% with respect to the ATCC 13032 lysC$^{T311I}$ strain can be determined for the production of L-lysine.

According to the invention, a gene having identity of at least 70% with the gene according to SEQ ID NO: 1, encoding for a pyruvate carboxylase, is provided which, starting from the gene having at least 70% identity with SEQ ID NO: 1 in position 1027-1029, has an exchange of the encoding triplet for threonine-343 for a triplet for alanine. Therefore, position 1027-1029 encodes for alanine. The DNA according to the invention comprises sequences of 70% to 100% identity. Preferably, the identity is 80%, 85% to 90%, Particularly preferably 91%, 92%, 93%, 94%, 95%, 96%, 97%, 98%, or 99%. Special preference is given to the gene according to SEQ ID NO: 1.

In a preferred embodiment, a gene with identity of at least 70% with the gene according to SEQ ID NO: 1, encoding for a pyruvate carboxylase, is provided which, starting from the gene having at least 70% identity with SEQ ID NO: 1, additionally has a triplet in position 3034-3036 which codes for serine. Also included in this embodiment are sequences of 70% to 100% identity. Preferably, the identity is 80%, 85% to 90%, particularly preferably 91%, 92%, 93%, 94%, 95%, 96%, 97%, 98%, or 99%. Special preference is given to the gene according to SEQ ID NO: 2

Identity as used herein can be defined by the equation I (%)=[1−V/X]×100, where I is identity, X is the total number of nucleobases of the comparison sequence, and V is the number of different nucleobases of the sequence to be observed relative to the comparison sequence. In any event, the term nucleic acid sequences which encode for polypeptides includes all sequences that appear possible according to the degeneration of the genetic code.

Furthermore, according to the invention, a vector, preferably a plasmid, is provided that contains this gene encoding for a pyruvate carboxylase with the T343A or T343A and I1012S modification. In principle, each empty vector or each empty plasmid can thereby be considered as an output vector or starting plasmid. For example, the plasmid pAN6 as described in the publication by Frunzke et al., Molecular Microbiology 2008, 67:305-322, into which a gene according to the invention is inserted, can be used as the empty vector.

According to the invention, a chromosome is also provided which contains the DNA according to the invention with the T343A or T343A and I1012S modification. The DNA can, according to the invention, be inserted into the chromosome in such a way that the function of the genes relevant to the viability of the microorganism is not impaired or destroyed.

By expression of the gene according to SEQ ID NO: 1, a pyruvate carboxylase according to the invention can be obtained having a sequence identity of at least 90% with respect to the pyruvate carboxylase according to SEQ ID NO: 3 wherein, starting from the pyruvate carboxylase of the ATCC 13032 lysC$^{T311I}$ strain, the threonine at position 343 is exchanged for alanine (pycT$^{343A}$). Therefore, alanine, according to the invention, can be located in position 343 of the pyruvate carboxylase, as, for example, in Seq. No. 3. Pyruvate carboxylase according to the invention comprises pyruvate carboxylases of 90% to 100% identity with respect to SEQ ID NO: 3. Preferably, the identity is 95%, 96%, or 97%, more preferably 98% or 99%, of the pyruvate carboxylase of SEQ ID NO: 3 that has been modified according to the invention. Special preference is given to the pyruvate carboxylase according to SEQ ID NO: 3.

By expression of the gene according to SEQ ID NO: 2, a pyruvate carboxylase according to the invention having a sequence identity of at least 90% with respect to the pyruvate carboxylase according to SEQ ID NO: 4 can be obtained wherein, starting from the pyruvate carboxylase of the ATCC 13032 lysC$^{T311I}$ strain, the threonine in position 343 is exchanged for alanine, and in addition the isoleucine at position 1012 is exchanged for serine (pyc$^{T343A;I1012S}$). Thus, according to the invention, alanine can be located in position 343 of the pyruvate carboxylase, and serine can be located in position 1012. Pyruvate carboxylase according to the invention can include pyruvate carboxylases of 90% to 100% identity with respect to SEQ ID NO: 4. Preferably, the identity is 95%, 96% or 97%, more preferably 98% or 99%, of the modified pyruvate carboxylase of SEQ ID NO: 4 according to the invention. Special preference can be given to the pyruvate carboxylase according to SEQ ID NO: 4.

The term identity as used herein can be defined by the equation I (%)=[1−V/X]*100, where I is identity, X is the total number of amino acids of the comparison sequence, and V is the number of different amino acids of the sequence to be observed relative to the comparison sequence. The following sequences are listed in the sequencing listing:

SEQ ID NO: 1: DNA sequence of the plasmid-based variant modified according to the invention, encoding for the pyruvate carboxylase pyc$^{T343A}$ modified according to the invention.

SEQ ID NO: 2: DNA sequence of the plasmid-based variant modified according to the invention, encoding for the pyruvate carboxylase pyc$^{T343A;I1012S}$ modified according to the invention.

SEQ ID NO: 3: Amino acid sequence of the pyruvate carboxylase Pyc-T343A modified according to the invention.

SEQ ID NO: 4: Amino acid sequence of the pyruvate carboxylase Pyc-T343A;I1012S modified according to the invention.

SEQ ID NO: 5: DNA sequence of the reference strain ATCC 13032 lysC$^{T311I}$ for the wild-type pyruvate carboxylase.

SEQ ID NO: 6: Amino acid sequence of the pyruvate carboxylase of the reference strain ATCC 13032 lysC$^{T311I}$ for the wild-type pyruvate carboxylase.

SEQ ID NO: 7: DNA sequence of the chromosomal variant DNA-pyc-A1027G-T1035G according to the invention, encoding for Pyc-T343A.

SEQ ID NO: 8: DNA sequence of the chromosomal variant DNA-pyc-A1027G-T1035G-T3035G-C3039G according to the invention, encoding for Pyc-T343A; I1012S.

In an advantageous development of the invention, the expression of the genes according to the invention can be amplified. For example, but not by way of limitation, to this end stronger promoters may be used, the number of gene copies may be increased, or the ribosome binding site may be modified to increase translation of the messenger RNA. The methods to be used for implementing these methods are known to the person skilled in the art.

Furthermore, a microorganism which contains a gene according to the invention or a vector according to the invention is a subject matter of the invention. This microorganism is preferably a coryneform bacterium. For example, *Corynebacterium glutamicum, Corynebacterium acetoglutamicum, Corynebacterium acetoacidophilum, Corynebacterium melassecola, Corynebacterium thermoaminogenes, Corynebacterium efficiens, Brevibacterium flavum,* or *Brevibacterium lactofermentum* may be specified as coryneform bacteria.

Particularly preferred cells according to the invention are those of the genera *Corynebacterium, Brevibacterium, Escherichia, Bacillus, Lactobacillus, Lactococcus, Zymomonas, Methylobacterium, Ralstonia, Clostridium, Candida, Pichia, Kluyveromyces, Saccharomyces,* and *Yarrowia,* wherein *Corynebacterium glutamicum, Corynebacterium efficiens, Brevibacterium flavum, Brevibacterium lactofermentum, Escherichia coli, Saccharomyces cerevisiae, Kluyveromyces lactis, Candida blankii, Candida rugosa, Zymomonas mobilis, Yarrowia lipolytica, Methylobacterium extorquens, Ralstonia eutropha,* and *Pichia pastoris* are particularly preferred. According to the invention, the most preferred cells are those of the genus *Corynebacterium* and

*Escherichia*, wherein *Corynebacterium glutamicum* and *Escherichia coli* are the especially preferred bacterial strains.

Especially in the event in which the product is L-lysine, the genetically modified cells may be derived in particular from cells selected from the group comprising *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium ammoniagenes flavum* ATCC14067, *Brevibacterium lactofermentum* ATCC13869, and *Brevibacterium divaricatum* ATCC14020, and mutants or strains prepared therefrom that produce L-amino acids, such as for example the L-lysine producing strains *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, and *Corynebacterium glutamicum* DSM 5715, or such as the *Corynebacterium glutamicum* ATCC21608 strain producing L-methionine, for example. *Escherichia coli* AJ11442 (see JP 56-18596 and U.S. Pat. No. 4,346,170), *Escherichia coli* strain VL611, and *Escherichia coli* strain WC196 (see WO-A-96/17930) are cited as examples of suitable *Escherichia coli* strains.

According to the invention, a method is provided for the production of products whose biosynthesis includes oxaloacetate as a precursor.

To this end, a microorganism containing a gene encoding for the pyruvate carboxylase, with the genetic modification encoding for the exchange T343A or two exchanges T343A and I1012S in the protein, is used for the production of metabolic products derived from oxaloacetate.

To this end, a gene with at least 70% identity with respect to the SEQ ID NO: 1, in which at positions 1027-1029 the triplet encoding for threonine is exchanged for a triplet encoding for alanine; or a gene with at least 70% identity with respect to SEQ ID NO: 2, in which at positions 1027-1029 the triplet encoding for threonine is exchanged for a triplet encoding for alanine, and in addition at position 3034-3036 the triplet encoding for isoleucine is exchanged for a triplet encoding for serine, is introduced into the microorganism.

The method according to the invention includes the use of a gene having at least 70% to 100% identity with respect to the gene according to SEQ ID NO: 1 or 2.

Preferably, a microorganism having a gene with identity of at least 80% to 90% with respect to SEQ ID NO: 1 or SEQ ID NO: 2 is used. Particularly preferably, a gene with identity of 91%, 92%, 93%, 94%, 95%, 96%, 97%, 98% or 99% with respect to SEQ ID NO: 1 or SEQ ID NO: 2 is used for the production method. Special preference is given to the gene according to SEQ ID NO: 1 or SEQ ID NO: 2.

The encoding gene used according to the invention for the pyruvate carboxylase may thereby be used chromosomally or in a vector, preferably in a plasmid.

The gene is expressed, and the pyruvate carboxylase according to the invention with identity of at least 90% with respect to the pyruvate carboxylase according to SEQ ID NO: 3, in which threonine is exchanged for alanine at position 343, has the effect of the increased production of oxaloacetate-derived metabolic products.

The expression of the pyruvate carboxylase according to the invention with identity of at least 90% with respect to the pyruvate carboxylase according to SEQ ID NO: 4, in which threonine is exchanged for alanine at position 343 and isoleucine is exchanged for serine at position 1012, has the effect of the increased production of oxaloacetate-derived metabolic products.

The method according to the invention includes the use of a pyruvate carboxylase having 90% to 100% identity with respect to the pyruvate carboxylase according to SEQ ID NO: 3 and SEQ ID NO: 4.

Preferably, the identity of the pyruvate carboxylase used according to the invention is 95%, 96%, or 97%, particularly preferably 98% or 99%, with respect to SEQ ID NO: 3 or 4. The use of pyruvate carboxylase according to SEQ ID NO: 3 is particularly preferred. Special preference is given to the use of pyruvate carboxylase according to SEQ ID NO: 4.

In a preferred embodiment, the gene according to the invention is more strongly expressed.

The microorganisms thus obtained can be fermented.

Preferably, an organism from the group consisting of the genera *Corynebacterium, Brevibacterium, Escherichia, Bacillus, Lactobacillus, Lactococcus, Zymomonas, Methylobacterium, Ralstonia, Clostridium, Candida, Pichia, Kluyveromyces, Saccharomyces,* and *Yarrowia* can be used as a production organism, wherein *Corynebacterium glutamicum, Corynebacterium efficiens, Brevibacterium flavum, Brevibacterium lactofermentum, Escherichia coli, Saccharomyces cerevisiae, Kluyveromyces lactis, Candida blankii, Candida rugosa, Zymomonas mobilis, Yarrowia lipolytica, Methylobacterium extorquens, Ralstonia eutropha,* and *Pichia pastoris* are particularly preferred. According to the invention, the most preferred cells are those of the genus *Corynebacterium* and *Escherichia*, wherein *Corynebacterium glutamicum* and *Escherichia coli* are especially preferred bacterial strains.

Especially in the instance in which the metabolite is L-lysine, the genetically modified cells or microorganisms can be derived in particular from cells selected from the group comprising *Corynebacterium glutamicum* ATCC13032, *Corynebacterium acetoglutamicum* ATCC15806, *Corynebacterium acetoacidophilum* ATCC13870, *Corynebacterium melassecola* ATCC 17965, *Corynebacterium thermoaminogenes* FERM BP-1539, *Brevibacterium ammoniagenes flavum* ATCC14067, *Brevibacterium lactofermentum* ATCC13869, and *Brevibacterium divaricatum* ATCC14020, and mutants or strains prepared therefrom producing L-amino acids, such as for example the L-lysine producing strains *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, and *Corynebacterium glutamicum* DSM 5715, or such as the *Corynebacterium glutamicum* ATCC21608 strain producing L-methionine, for example. *Escherichia coli* AJ11442 (see JP 56-18596 and U.S. Pat. No. 4,346,170), *Escherichia coli* strain VL611, and *Escherichia coli* strain WC196 (see WO-A-96/17930) are used as examples of suitable *Escherichia coli* strains.

With methods according to the invention, in particular amino acids of the aspartate family may be increased, that is to say that L-lysine, L-aspartate, L-asparagine, L-threonine, L-isoleucine and L-methionine may be produced. Furthermore, the production of amino acids of the glutamate family, such as L-glutamate, L-glutamine, L-arginine, or L-proline; of intermediates of the citrate cycle such as, for example, succinate, fumarate, malate, citrate, isocitrate, or 2-oxoglutarate; of diamines, for example diaminopentane or diaminobutane; or also of other products such as itaconate, ectoine, gamma-aminobutyrate, butanol, 1-propanol, L-citrulline, L-ornithine, D-arginine, or 4-hydroxyproline, may be increased.

The product produced by fermentation and secreted into the culture supernatant can then be enriched and isolated.

FIG. 1 shows the growth of the *C. glutamicum* ATCC 13032 lysC$^{T311I}$ strain with the chromosomally encoded Pyc variants Pyc$^{T343A}$ and Pyc$^{T343A;I1012S}$. In FIG. 1, the abscissa shows the time in hours (h) and the ordinate shows the value for backscatter at 620 nm (a.u.) as a measure of cell density. The *C. glutamicum* ATCC 13032 lysC$^{T311I}$ strain with native Pyc, that is to say with threonine at position 343 and isoleucine at position 1012, served as a control. All strains were cultivated in CGXII minimal medium with 4% (wt/vol) glucose in a BioLector® system at 30° C. and 1200 rpm for 24 hours.

Figure 2:
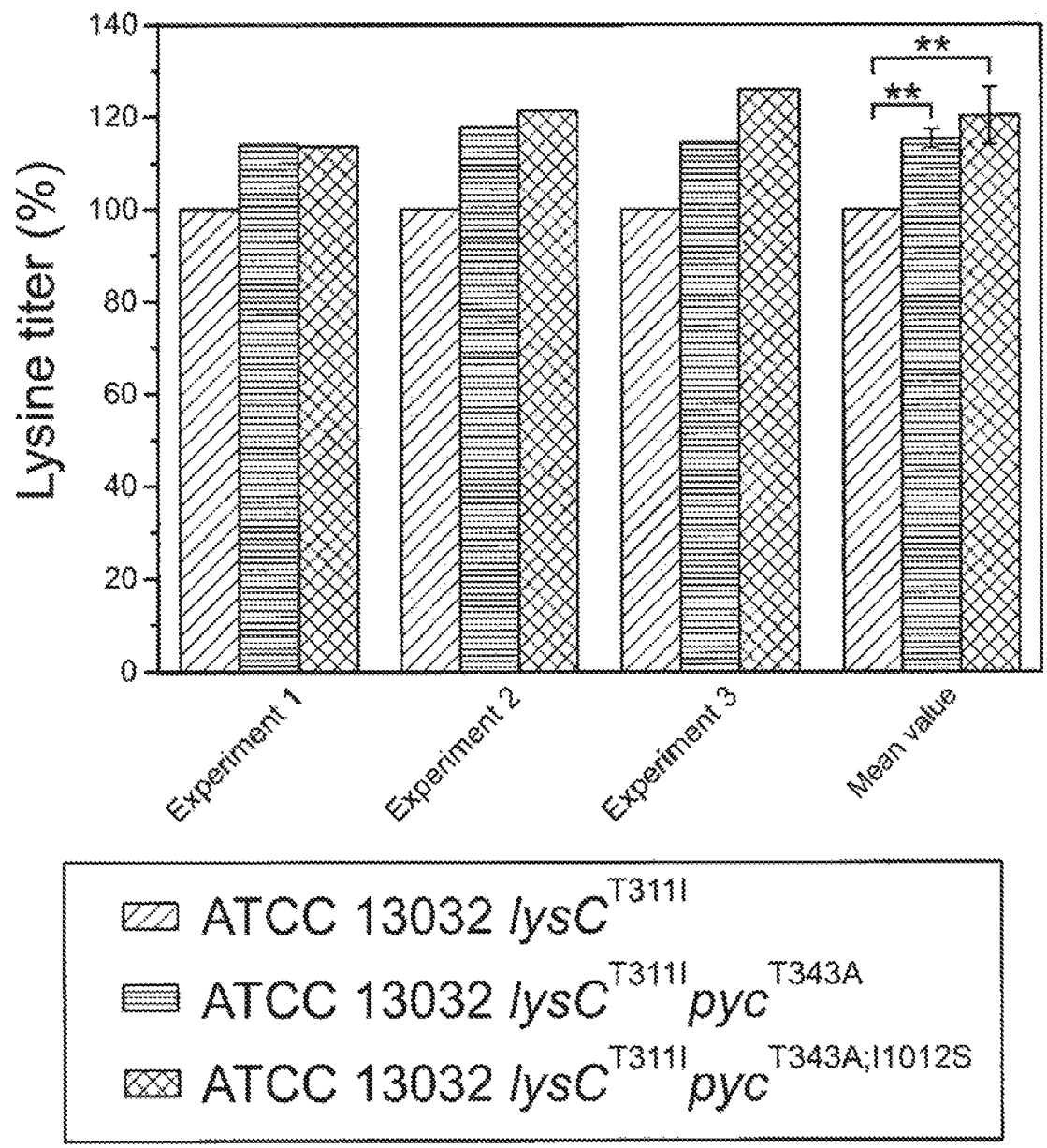
FIG. 2 illustrates L-lysine production of the strains *C. glutamicum* ATCC 13032 lysc$^{T311I}$, *C. glutamicum* ATCC 13032 lysC$^{T311I}$ with chromosomally encoded Pyc$^{T343A}$, as well as *C. glutamicum* ATCC 13032 lysC$^{T311I}$ with chromosomally encoded Pyc$^{T343A;I1012S}$.

FIG. 2 shows the L-lysine production of the *C. glutamicum* ATCC 13032 lysC$^{T311I}$ strains with the chromosomally encoded Pyc variant PycT343A and with the chromosomally encoded Pyc variant Pyc$^{T343A;I1012S}$ Therein, the abscissa indicates three independent replicates and the mean value from the three experiments, and the ordinate indicates the percentile lysine concentration, wherein the lysine concentration of the ATCC 13032 lysC$^{T311I}$ control strain (black bars) was respectively set as 100% in the three independent replicates. The L-lysine concentrations for the ATCC 13032 lysC$^{T311I}$ pyc$^{T343A}$ strain are shown as obliquely hatched bars. The L-lysine concentrations for the ATCC 13032 lysC$^{T311I}$ pyc$^{T343A;I1012S}$ strain are shown as horizontally hatched bars. After cultivating the cells in a Biolector® system for 24 h (see FIG. 1), the cells were harvested and the L-lysine concentration in the supernatant of the respective cultures was determined via reversed phase HPLC with ortho-phthaldialdehyde derivatization. In each of the three replicates, both the strain with the mutated Pyc variant Pyc$^{T343A}$ and the strain with the mutated Pyc variant Pyc$^{T343A;I1012S}$ exhibited a higher lysine titer than the comparative strain with native Pyc. An increase in the final L-lysine concentration by an average of 15-19% relative to *C. glutamicum* ATCC 12032 lysC$^{T311I}$ is to be observed. The measured lysine concentrations of the individual mutants were compared by t-test. The asterisks shown in the illustration represent p≤0.01.

Figure 3:
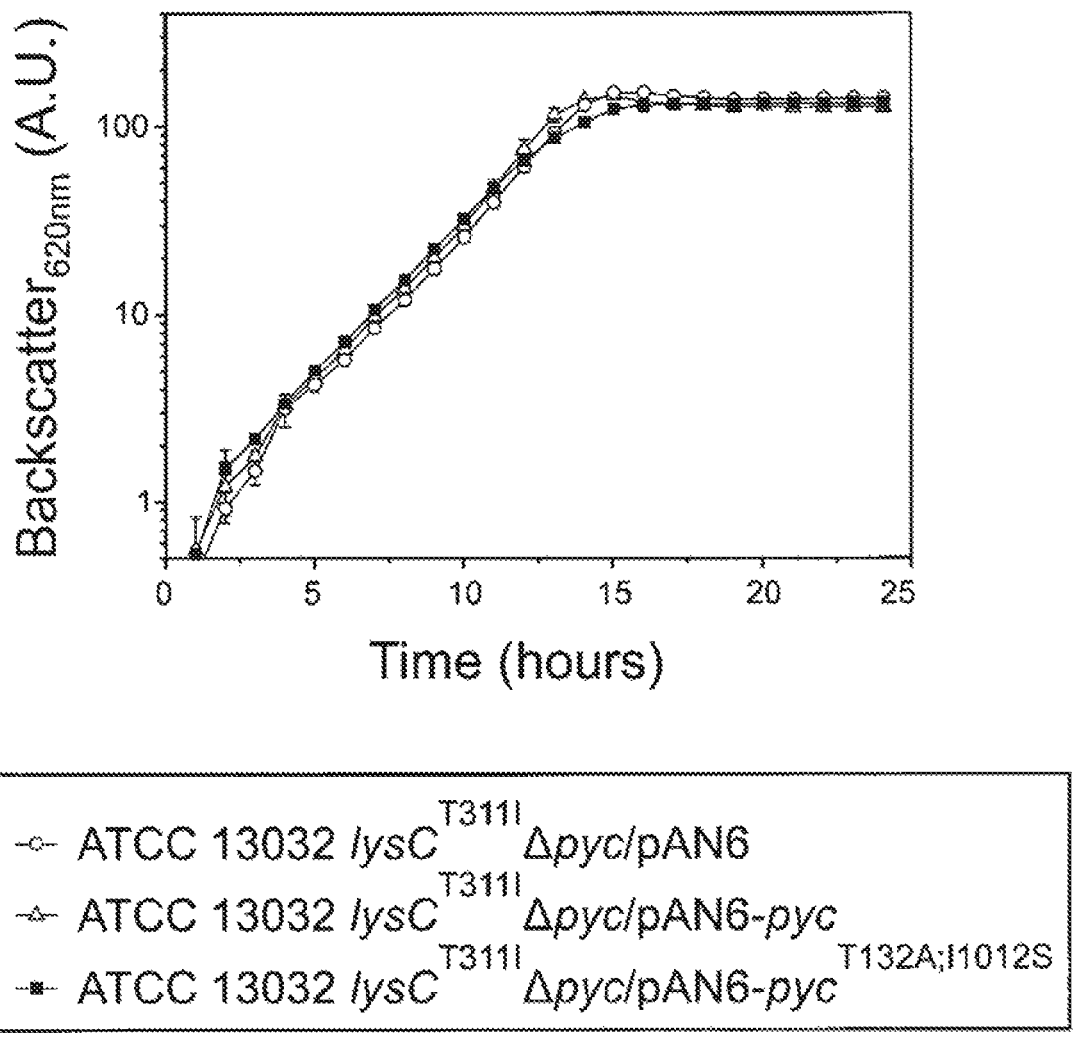
FIG. 3 illustrates growth of *C. glutamicum* ATCC 13032 lysC$^{T311I}$ Δpyc with the plasmid pAN6-pyc$^{T343A;I1012S}$.

FIG. 3 shows the growth of the *C. glutamicum* 13032 lysC$^{T311I}$ Δpyc strain with the plasmid pAN6-pyc$^{T343A;I1012S}$ Again, in the Figure the abscissa shows the time in hours (h) and the ordinate shows the value for backscatter at 620 nm (a.u.). For control purposes, the *C. glutamicum* ATCC 13032 lysC$^{T311I}$ Δpyc strains, which carry either the empty plasmid pAN6 or the plasmid pAN6-pyc with native pyc, were entrained. All strains were cultivated in CGXII minimal medium with 4% (wt/vol) glucose and 25 mg L$^{-1}$ kanamycin in a BioLector® system at 30° C. and 1200 rpm for 24 hours. At the start of cultivation, the expression of pyc was induced with 1 mM IPTG (isopropyl-β-D-thiogalactoside).

Figure 4:
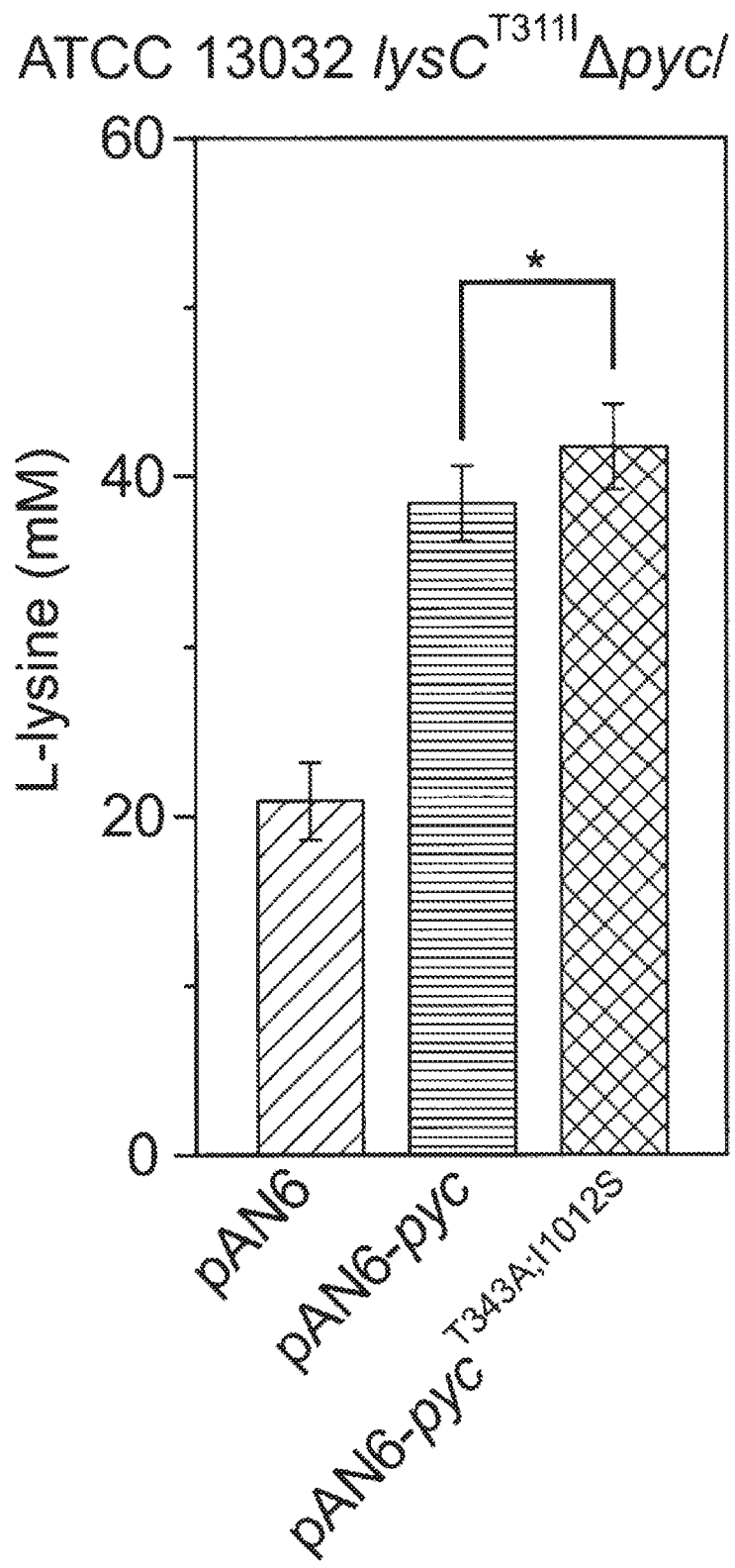
FIG. 4 illustrates L-lysine production of the *C. glutamicum* ATCC 13032 lysC$^{T311I}$ Δpyc strain with the plasmid pAN6-pyc$^{T343A;I1012S}$.

FIG. 4 shows the L-lysine production of the *C. glutamicum* ATCC 13032 lysC$^{T311I}$ Δpyc strain with the plasmid pAN6-pyc$^{T343A;I1012S}$. Therein, the abscissa indicates the *C. glutamicum* ATCC 13032 lysC$^{T311I}$ Δpyc strain containing the empty vector pAN6 (hatched bar), the vector pAN6-pyc with native pyruvate carboxylase (white bar), or the vector pAN6-pyc$^{T343A;I1012S}$ (black bar) in comparison. After cultivating the cells in a Biolector® system for 24 h (see FIG. 3), the cells were harvested and the L-lysine concentration in the supernatant of the respective cultures was determined via reversed phase HPLC with ortho-phthaldialdehyde derivatization. As a comparison, the lysine production in the *C. glutamicum* 13032 lysC$^{T311I}$ Δpyc/pAN6 strain (without Pyc) and ATCC 13032 lysC$^{T311I}$/pAN6-pyc (with native pyc) was measured. The present data represent mean values and standard deviations from at least six biological replicates. The measured lysine concentrations of the individual mutants were compared by t-test. The asterisk shown in the Figure thereby represents p≤0.05. A marked increase in the final L-lysine concentration of 9% is evident in the strain with the Pyc$^{T343A;I1012S}$ variant compared to the strain with native Pyc.

Within the scope of the invention, a mutation in the pyc gene could be identified which leads to an increased L-lysine production. A plasmid-based Pyc mutant library was first created by means of error-prone PCR, which was subsequently screened for increased fluorescence in the ATCC1303 lysC$^{T311I}$ Δpyc with the aid of a genetically encoded lysine sensor (pSenLys) and fluorescence-activated cell sorting (FACS). The isolated cells were subsequently multiplied and tested for increased lysine formation. These methods are known to the person skilled in the art (cf. Binder et al., genome Biol. 2012, 13:R40). The gene and enzyme variants that were thereby isolated were genetically characterized, leading ultimately to the identification of the Pyc variant according to the invention which increases the production of L-lysine as well as other oxaloacetate-derived metabolites. The found mutations are T343A and T343A; I1012S.

1. Chromosomally Encoded Pyc Variant Pyc T343A:

Measurement of the L-lysine production of *C. glutamicum* ATCC 13032 lysC$^{T311I}$ with the chromosomally encoded Pyc variant Pyc T343A:

The exchange of the threonine codon 343 in the chromosomal pyc gene for an alanine codon was accomplished by two-fold homologous recombination using the vector pK19mobsacB by methods known to the person skilled in the art (Schafer et al., 1994 Gene 145:69-73; Hochheim et al., 2017 Biotechnol Lett 39:283-288). The production was compared with the *C. glutamicum* ATCC 13032 lysC$^{T311I}$ strain with native chromosomal pyc gene. The strains were cultivated in 800 pl CGXII minimal medium with 4% (wt/vol) glucose for 24 h in a Biolector system at 30° C. and 1200 rpm (FIG. 1). The start OD at 600 nm was 0.5. After 24 h, the cells of the individual cultures were sedimented and the L-lysine concentration in the supernatant was measured. The measurement was performed via reversed phase HPLC with a precolumn derivatization of the amino acids over ortho-phthaldialdehyde. A gradient of 80% solution A (100 mM sodium acetate (pH 7.2)) and 20% solution B (100% (vol/vol) methanol) to 20% solution A and 80% solution B was used as mobile phase. The example shows that the examined Pyc variant has a positive effect on lysine production, and this can be increased by up to 15% if the Pyc variant Pyc T343A is chromosomally encoded instead of the wild-type Pyc protein.

2. Chromosomally Encoded Pyc Variant Pyc T343A; I1012S:

Measurement of the L-lysine production of *C. glutamicum* ATCC 13032 lysC$^{T311I}$ with the chromosomally encoded Pyc variant Pyc T343A;I1012S:

The exchange of the threonine codon 343 for an alanine codon, and of the isoleucine codon 1012 for a serine codon, in the chromosomal pyc gene was accomplished by two-fold homologous recombination using the vector pK19mobsacB by methods known to the person skilled in the art (Schafer et al., 1994 Gene 145:69-73; Hochheim et al., 2017 Biotechnol Lett 39:283-288). The production was compared with the *C. glutamicum* ATCC 13032 lysC$^{T311I}$ strain with native chromosomal pyc gene. The strains were cultivated in 800 pl CGXII minimal medium with 4% (wt/vol) glucose for 24 h in a Biolector system at 30° C. and 1200 rpm (FIG. 1). The start OD at 600 nm was 0.5. After 24 h, the cells of the individual cultures were sedimented and the L-lysine concentration in the supernatant was measured. The measurement was performed via reversed phase HPLC with a precolumn derivatization of the amino acids over ortho-phthaldialdehyde. A gradient of 80% solution A (100 mM sodium acetate (pH 7.2)) and 20% solution B (100% (vol/vol) methanol) to 20% solution A and 80% solution B was used as mobile phase. The example shows that the examined Pyc variant has a positive effect on lysine production, and this can be increased by up to 19% if the Pyc variant Pyc T343A;I1012S is chromosomally encoded instead of the wild-type Pyc protein.

3. Plasmid-Encoded Pyc Variant Pyc T343A;I1012S:

Measurement of the L-lysine production of *C. glutamicum* ATCC 13032 lysC$^{T311I}$ Δpyc/pAN6-pyc$^{T343A;I1012S}$.

Production with the *C. glutamicum* 13032 lysC$^{T311I}$ Δpyc/pAN6-pyc strain encoding the native Pyc and with the empty plasmid control *C. glutamicum* 13032 lysC$^{T311I}$ Δpyc/pAN6 was compared. The strains were cultivated in 800 pl CGXII minimal medium with 4% (wt/vol) glucose and 25 mg/l kanamycin for 24 h in a Biolector system at 30° C. and 1200 rpm (FIG. 3). The start OD at 600 nm was 0.5. After 24 h, the cells of the individual cultures were sedimented and the L-lysine concentration in the supernatant was measured. The measurement was performed via reversed phase HPLC with a precolumn derivatization of the amino acids over ortho-phthaldialdehyde. A gradient of 80% solution A (100 mM sodium acetate (pH 7.2)) and 20% solution B (100% (vol/vol) methanol) to 20% solution A and 80% solution B was used as mobile phase. The example shows that lysine production can be increased by up to 9% if the Pyc variant Pyc$^{T343A;I1012S}$ is encoded on the plasmid pAN6 instead of the wild-type Pyc. (FIG. 4)

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. An isolated DNA sequence encoding a pyruvate carboxylase, comprising:
   at least 97% identity with respect to SEQ ID NO: 1,
   wherein a triplet at position 1027-1029 codes for alanine.
2. The DNA sequence according to claim 1, wherein the DNA has identity of at least 99% with respect to SEQ ID NO: 1.
3. The DNA sequence according to claim 1, wherein the DNA sequence is a DNA according to SEQ ID NO: 1.
4. The DNA sequence according to claim 1, further comprising, at position 3034-3036, a triplet which encodes for serine.
5. The DNA sequence according to claim 4, wherein the DNA has identity of at least 97% with respect to SEQ ID NO: 2.
6. The DNA sequence according to claim 4, wherein the DNA is according to SEQ ID NO: 2.
7. A pyruvate carboxylase having at least 97% identity with respect to a pyruvate carboxylase according to SEQ ID NO: 3, wherein alanine is present at position 343.
8. The pyruvate carboxylase according to claim 7, wherein the pyruvate carboxylase has identity of at least 99% with respect to the pyruvate carboxylase according to SEQ ID NO: 3.
9. The pyruvate carboxylase according to claim 7, wherein the pyruvate carboxylase is a pyruvate carboxylase according to SEQ ID NO: 3.
10. The pyruvate carboxylase according to claim 7, further comprising serine at position 1012.
11. The pyruvate carboxylase according to claim 10, wherein the pyruvate carboxylase has identity of at least 97% with respect to the pyruvate carboxylase according to SEQ ID NO: 4.
12. The pyruvate carboxylase according to claim 10, wherein the pyruvate carboxylase is a pyruvate carboxylase according to SEQ ID NO: 4.
13. A vector, wherein the vector comprises a DNA sequence according to claim 1.
14. The vector according to claim 13, wherein the vector is a plasmid.
15. A microorganism, wherein the microorganism comprises a DNA sequence according to claim 1.
16. The microorganism according to claim 15, wherein the microorganism comprises a vector.
17. The microorganism according to claim 15, wherein the microorganism is a microorganism selected from the group consisting of the genera *Corynebacterium, Brevibacterium, Bacillus, Lactobacillus, Lactococcus, Candida, Pichia, Kluyveromyces, Saccharomyces, Escherichia, Zymomonas, Yarrowia, Methylobacterium, Ralstonia, Vibrio*, and *Clostridium*.
18. A method for the production of products whose biosynthesis includes oxaloacetate as a precursor, the method comprising:
   fermenting a microorganism containing a DNA sequence according to claim 1, which forms a pyruvate carboxylase, and
   performing an enrichment of the products in a medium or in cells.
19. The method according to claim 18, wherein a product is isolated.
20. The method according to claim 18, wherein a species from the group consisting of the genera *Corynebacterium, Brevibacterium, Bacillus, Lactobacillus, Lactococcus, Candida, Pichia, Kluyveromyces, Saccharomyces, Escherichia, Zymomonas, Yarrowia, Methylobacterium, Ralstonia, Vibrio*, and *Clostridium* is used as the microorganism.
21. The method according to claim 18, wherein an amino acid of the aspartate family is produced.
22. The method according to claim 21, wherein L-lysine, L-aspartate, L-asparagine, L-threonine, L-isoleucine, or L-methionine is produced.
23. The method according to claim 18, wherein substances from the glutamate family of amino acids are produced, such as L-glutamate, glutamine, L-arginine, L-proline, L-citrulline, or L-ornithine; intermediates of the citrate cycle, such as malate, fumarate, succinate, malate, fumarate citrate, isocitrate, or 2-oxoglutarate; diamines, such as diaminopentane or diaminobutane; as well as further metabolites prepared from oxaloacetate, such itaconate, ectoine, gamma aminobutyrate, butanol, 1-propanol, L-citrulline, L-ornithine, D-arginine, or 4-hydroxyproline.
24. The method according to claim 18, wherein the DNA sequence is more strongly expressed.
25. A chromosome including the DNA sequence according to claim 1.

* * * * *

SEQUENCE LISTING

<160> NUMBER OF SEQ ID NOS: 8

<210> SEQ ID NO 1
<211> LENGTH: 3423
<212> TYPE: DNA
<213> ORGANISM: Corynebacterium glutamicum

<400> SEQUENCE: 1

```
atgtcgactc acacatcttc aacgcttcca gcattcaaaa agatcttggt agcaaaccgc      60
ggcgaaatcg cggtccgtgc tttccgtgca gcactcgaaa ccggtgcagc cacggtagct     120
atttaccccc gtgaagatcg gggatcattc caccgctctt ttgcttctga agctgtccgc     180
attggtaccg aaggctcacc agtcaaggcg tacctggaca tcgatgaaat tatcggtgca     240
gctaaaaaag ttaaagcaga tgccatttac ccgggatacg gcttcctgtc tgaaaatgcc     300
cagcttgccc gcgagtgtgc ggaaaacggc attactttta ttggcccaac cccagaggtt     360
cttgatctca ccggtgataa gtctcgcgcg gtaaccgccg cgaagaaggc tggtctgcca     420
gttttggcgg aatccacccc gagcaaaaac atcgatgaga tcgttaaaag cgctgaaggc     480 cagcttacc ccatctttgt gaaggcagtt gccggtggtg gcggacgcgg tatgcgtttt     540
gttgcttcac ctgatgagct tcgcaaatta gcaacagaag catctcgtga agctgaagcg     600
gctttcggcg atggcgcggt atatgtcgaa cgtgctgtga ttaaccctca gcatattgaa     660
gtgcagatcc ttgcgatca cactggagaa gttgtacacc tttatgaacg tgactgctca     720
ctgcagcgtc gtcaccaaaa agttgtcgaa attgcgccag cacagcattt ggatccagaa     780
ctgcgtgatc gcatttgtgc ggatgcagta aagttctgcc gctccattgg ttaccagggc     840
```

```
gcgggaaccg tggaattctt ggtcgatgaa aagggcaacc acgtcttcat cgaaatgaac      900
ccacgtatcc aggttgagca caccgtgact gaagaagtca ccgaggtgga cctggtgaag      960
gcgcagatgc gcttggctgc tggtgcaacc ttgaaggaat gggtctgac ccaagataag      1020 atcaaggccc acggtgcagc actgcagtgc cgcatcacca cggaagatcc aaacaacggc      1080
ttccgcccag ataccggaac tatcaccgcg taccgctcac caggcggagc tggcgttcgt      1140
cttgacggtg cagctcagct cggtggcgaa atcaccgcac actttgactc catgctggtg      1200
aaaatgacct gccgtggttc cgactttgaa actgctgttg ctcgtgcaca gcgcgcgttg      1260
gctgagttca ccgtgtctgg tgttgcaacc aacattggtt tcttgcgtgc gttgctgcgg      1320
gaagaggact tcacttccaa gcgcatcgcc accggattca ttgccgatca cccgcacctc      1380
cttcaggctc cacctgctga tgatgagcag ggacgcatcc tggattactt ggcagatgtc      1440
accgtgaaca agcctcatgg tgtgcgtcca aaggatgttg cagctcctat cgataagctg      1500
cctaacatca aggatctgcc actgccacgc ggttcccgtg accgcctgaa gcagcttggc      1560
ccagccgcgt ttgctcgtga tctccgtgag caggacgcac tggcagttac tgataccacc      1620
ttccgcgatg cacaccagtc tttgcttgcg acccgagtcc gctcattcgc actgaagcct      1680
gcggcagagg ccgtcgcaaa gctgactcct gagcttttgt ccgtggaggc ctgggcggc      1740 gcgacctacg atgtggcgat gcgtttcctc tttgaggatc cgtgggacag gctcgacgag      1800
ctgcgcgagg cgatgccgaa tgtaaacatt cagatgctgc ttcgcggccg caacaccgtg      1860
ggatacaccc cgtacccaga ctccgtctgc cgcgcgtttg ttaaggaagc tgccagctcc      1920
ggcgtggaca tcttccgcat cttcgacgcg cttaacgacg tctcccagat cgtccagca      1980 atcgacgcag tcctggagac caacaccgcg gtagccgagg tggctatggc ttattctggt      2040
gatctctctg atccaaatga aaagctctac accctggatt actacctaaa gatggcagag      2100
gagatcgtca gtctggcgc tcacatcttg gccattaagg atatggctgg tctgcttcgc      2160
ccagctgcgg taaccaagct ggtcaccgca ctgcgccgtg aattcgatct gccagtgcac      2220
gtgcacaccc acgacactgc gggtggccag ctggcaacct actttgctgc agctcaagct      2280
ggtgcagatg ctgttgacgg tgcttccgca ccactgtctg gcaccacctc ccagccatcc      2340
ctgtctgcca ttgttgctgc attgcgcgcac accgtcgcg ataccggttt gagcctcgag      2400
gctgtttctg acctcgagcc gtactgggaa gcagtgcgcg gactgtacct gccatttgag      2460
tctggaaccc caggcccaac cggtcgcgtc taccgccacg aaatcccagg cggacagttg      2520
tccaacctgc gtgcacaggc caccgcactg gccttgcgg atcgtttcga actcatcgaa      2580
gacaactacg cagccgttaa tgagatgctg ggacgcccaa ccaaggtcac cccatcctcc      2640
aaggttgttg cgcacctcgc actccacctc gttggtgcgg gtgtggatcc agcagacttt      2700
gctgccgatc cacaaaagta cgacatccca gactctgtca tcgcgttcct gcgcggcgag      2760
cttggtaacc ctccaggtgg ctggccagag ccactgcgca cccgcgcact ggaaggccgc      2820
tccgaaggca aggcacctct gacggaagtt cctgaggaag agcaggcgca cctcgacgct      2880
gatgattcca aggaacgtcg caatagcctc aaccgcctgc tgttcccgaa gccaaccgaa      2940
gagttcctcg agcaccgtcg ccgcttcggc aacacctctg cgctggatga tcgtgaattc      3000
ttctacggcc tggtcgaagg ccgcgagact ttgatccgcc tgccagatgt gcgcaccca      3060 ctgcttgttc gcctggatgc gatctctgag ccagacgata agggtatgcg caatgttgtg      3120
gccaacgtca acggccagat ccgcccaatg cgtgtgcgtg accgctccgt tgagtctgtc      3180
```

| | |
|---|---|
| accgcaaccg cagaaaaggc agattcctcc aacaagggcc atgttgctgc accattcgct | 3240 |
| ggtgttgtca ccgtgactgt tgctgaaggt gatgaggtca aggctggaga tgcagtcgca | 3300 |
| atcatcgagg ctatgaagat ggaagcaaca atcactgctt ctgttgacgg caaaatcgat | 3360 |
| cgcgttgtgg ttcctgctgc aacgaaggtg gaaggtggcg acttgatcgt cgtcgtttcc | 3420 |
| taa | 3423 |

<210> SEQ ID NO 2
<211> LENGTH: 3423
<212> TYPE: DNA
<213> ORGANISM: Corynebacterium glutamicum

<400> SEQUENCE: 2

| | |
|---|---|
| atgtcgactc acacatcttc aacgcttcca gcattcaaaa agatcttggt agcaaaccgc | 60 |
| ggcgaaatcg cggtccgtgc tttccgtgca gcactcgaaa ccggtgcagc cacggtagct | 120 |
| atttaccccc gtgaagatcg gggatcattc caccgctctt ttgcttctga agctgtccgc | 180 |
| attggtaccg aaggctcacc agtcaaggcg tacctggaca tcgatgaaat tatcggtgca | 240 |
| gctaaaaaag ttaaagcaga tgccatttac ccgggatacg gcttcctgtc tgaaaatgcc | 300 |
| cagcttgccc gcgagtgtgc ggaaaacggc attactttta ttggcccaac cccagaggtt | 360 |
| cttgatctca ccggtgataa gtctcgcgcg gtaaccgccg cgaagaaggc tggtctgcca | 420 |
| gttttggcgg aatccacccc gagcaaaaac atcgatgaga tcgttaaaag cgctgaaggc | 480 |
| cagacttacc ccatctttgt gaaggcagtt gccggtggtg gcggacgcgg tatgcgtttt | 540 |
| gttgcttcac ctgatgagct tcgcaaatta gcaacagaag catctcgtga agctgaagcg | 600 |
| gctttcggcg atggcgcggt atatgtcgaa cgtgctgtga ttaaccctca gcatattgaa | 660 |
| gtgcagatcc ttggcgatca cactggagaa gttgtacacc tttatgaacg tgactgctca | 720 |
| ctgcagcgtc gtcaccaaaa agttgtcgaa attgcgccag cacagcattt ggatccagaa | 780 |
| ctgcgtgatc gcatttgtgc ggatgcagta aagttctgcc gctccattgg ttaccagggc | 840 |
| gcgggaaccg tggaattctt ggtcgatgaa aagggcaacc acgtcttcat cgaaatgaac | 900 |
| ccacgtatcc aggttgagca caccgtgact gaagaagtca ccgaggtgga cctggtgaag | 960 |
| gcgcagatgc gcttggctgc tggtgcaacc ttgaaggaat gggtctgac ccaagataag | 1020 |
| atcaaggccc acggtgcagc actgcagtgc cgcatcacca cggaagatcc aaacaacggc | 1080 |
| ttccgcccag ataccggaac tatcaccgcg taccgctcac caggcggagc tggcgttcgt | 1140 |
| cttgacggtg cagctcagct cggtggcgaa atcaccgcac actttgactc catgctggtg | 1200 |
| aaaatgacct gccgtggttc cgactttgaa actgctgttg ctcgtgcaca gcgcgcgttg | 1260 |
| gctgagttca ccgtgtctgg tgttcaacc aacattggtt tcttgcgtgc gttgctgcgg | 1320 |
| gaagaggact tcacttccaa gcgcatcgcc accggattca ttgccgatca cccgcacctc | 1380 |
| cttcaggctc cacctgctga tgatgagcag ggacgcatcc tggattactt ggcagatgtc | 1440 |
| accgtgaaca gcctcatgg tgtgcgtcca aaggatgttg cagctcctat cgataagctg | 1500 |
| cctaacatca aggatctgcc actgccacgc ggttcccgtg accgcctgaa gcagcttggc | 1560 |
| ccagccgcgt tgctcgtga tctccgtgag caggacgcac tggcagttac tgataccacc | 1620 |
| ttccgcgatg cacaccagtc tttgcttgcg acccgagtcc gctcattcgc actgaagcct | 1680 |
| gcggcagagg ccgtcgcaaa gctgactcct gagcttttgt ccgtggaggc ctggggcggc | 1740 |
| gcgacctacg atgtggcgat gcgttcctc tttgaggatc cgtgggacag gctcgacgag | 1800 |
| ctgcgcgagg cgatgccgaa tgtaaacatt cagatgctgc ttcgcggccg caacaccgtg | 1860 |

-continued

```
ggatacaccc cgtacccaga ctccgtctgc cgcgcgtttg ttaaggaagc tgccagctcc    1920
ggcgtggaca tcttccgcat cttcgacgcg cttaacgacg tctcccagat gcgtccagca    1980
atcgacgcag tcctggagac caacaccgcg gtagccgagg tggctatggc ttattctggt    2040
gatctctctg atccaaatga aaagctctac accctggatt actacctaaa gatggcagag    2100
gagatcgtca gtctggcgc tcacatcttg gccattaagg atatggctgg tctgcttcgc    2160
ccagctgcgg taaccaagct ggtcaccgca ctgcgccgtg aattcgatct gccagtgcac    2220
gtgcacaccc acgacactgc gggtggccag ctggcaacct actttgctgc agctcaagct    2280
ggtgcagatg ctgttgacgg tgcttccgca ccactgtctg caccacctc ccagccatcc     2340 ctgtctgcca ttgttgctgc attcgcgcac accgtcgcg ataccggttt gagcctcgag     2400
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgcgg atcgtttcga actcatcgaa    2580
gacaactacg cagccgttaa tgagatgctg ggacgcccaa ccaaggtcac cccatcctcc    2640
aaggttgttg cgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgagccgcc tgccagatgt gcgcacccca    3060
ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg gaaggtggcg acttgatcgt cgtcgtttcc    3420
taa                                                                   3423
```

<210> SEQ ID NO 3
<211> LENGTH: 1140
<212> TYPE: PRT
<213> ORGANISM: Corybebacterium glutamicum

<400> SEQUENCE: 3

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
```

```
            85                  90                  95
Ser Glu Asn Ala Gln Leu Ala Arg Glu Cys Ala Glu Asn Gly Ile Thr
            100                 105                 110
Phe Ile Gly Pro Thr Pro Glu Val Leu Asp Leu Thr Gly Asp Lys Ser
            115                 120                 125
Arg Ala Val Thr Ala Ala Lys Lys Ala Gly Leu Pro Val Leu Ala Glu
130                 135                 140
Ser Thr Pro Ser Lys Asn Ile Asp Glu Ile Val Lys Ser Ala Glu Gly
145                 150                 155                 160
Gln Thr Tyr Pro Ile Phe Val Lys Ala Val Ala Gly Gly Gly Gly Arg
                165                 170                 175
Gly Met Arg Phe Val Ala Ser Pro Asp Glu Leu Arg Lys Leu Ala Thr
            180                 185                 190
Glu Ala Ser Arg Glu Ala Glu Ala Ala Phe Gly Asp Gly Ala Val Tyr
            195                 200                 205
Val Glu Arg Ala Val Ile Asn Pro Gln His Ile Glu Val Gln Ile Leu
210                 215                 220
Gly Asp His Thr Gly Glu Val Val His Leu Tyr Glu Arg Asp Cys Ser
225                 230                 235                 240
Leu Gln Arg Arg His Gln Lys Val Val Glu Ile Ala Pro Ala Gln His
                245                 250                 255
Leu Asp Pro Glu Leu Arg Asp Arg Ile Cys Ala Asp Ala Val Lys Phe
            260                 265                 270
Cys Arg Ser Ile Gly Tyr Gln Gly Ala Gly Thr Val Glu Phe Leu Val
            275                 280                 285
Asp Glu Lys Gly Asn His Val Phe Ile Glu Met Asn Pro Arg Ile Gln
            290                 295                 300
Val Glu His Thr Val Thr Glu Glu Val Thr Glu Val Asp Leu Val Lys
305                 310                 315                 320
Ala Gln Met Arg Leu Ala Ala Gly Ala Thr Leu Lys Glu Leu Gly Leu
                325                 330                 335
Thr Gln Asp Lys Ile Lys Ala His Gly Ala Ala Leu Gln Cys Arg Ile
            340                 345                 350
Thr Thr Glu Asp Pro Asn Asn Gly Phe Arg Pro Asp Thr Gly Thr Ile
            355                 360                 365
Thr Ala Tyr Arg Ser Pro Gly Gly Ala Gly Val Arg Leu Asp Gly Ala
            370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
            435                 440                 445
Ile Ala Thr Gly Phe Ile Ala Asp His Pro His Leu Leu Gln Ala Pro
            450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
```

```
Arg Asp Arg Leu Lys Gln Leu Gly Pro Ala Ala Phe Ala Arg Asp Leu
    515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Ala Gln Ala Gly Ala Asp Ala Val Asp Gly Ala
    755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
                820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
            915                 920                 925
```

Pro Glu Pro Leu Arg Thr Arg Ala Leu Glu Gly Arg Ser Glu Gly Lys
            930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
                995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 4
<211> LENGTH: 1140
<212> TYPE: PRT
<213> ORGANISM: Corynebacterium glutamicum

<400> SEQUENCE: 4

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

```
Gln Thr Tyr Pro Ile Phe Val Lys Ala Val Ala Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
            195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
                260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
            290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Ala His Gly Ala Ala Leu Gln Cys Arg Ile
                340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575
```

-continued

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
            980                 985                 990

Ser Ala Leu Asp Asp Arg Glu Phe Phe Tyr Gly Leu Val Glu Gly Arg

|  | 995 |  |  |  | 1000 |  |  |  |  | 1005 |  |
|---|---|---|---|---|---|---|---|---|---|---|---|

Glu Thr Leu Ser Arg Leu Pro Asp Val Arg Thr Pro Leu Leu Val
      1010                    1015                    1020

Arg Leu Asp Ala Ile Ser Glu Pro Asp Asp Lys Gly Met Arg Asn
      1025                    1030                    1035

Val Val Ala Asn Val Asn Gly Gln Ile Arg Pro Met Arg Val Arg
      1040                    1045                    1050

Asp Arg Ser Val Glu Ser Val Thr Ala Thr Ala Glu Lys Ala Asp
      1055                    1060                    1065

Ser Ser Asn Lys Gly His Val Ala Ala Pro Phe Ala Gly Val Val
      1070                    1075                    1080

Thr Val Thr Val Ala Glu Gly Asp Glu Val Lys Ala Gly Asp Ala
      1085                    1090                    1095

Val Ala Ile Ile Glu Ala Met Lys Met Glu Ala Thr Ile Thr Ala
      1100                    1105                    1110

Ser Val Asp Gly Lys Ile Asp Arg Val Val Val Pro Ala Ala Thr
      1115                    1120                    1125

Lys Val Glu Gly Gly Asp Leu Ile Val Val Val Ser
      1130                    1135                    1140

<210> SEQ ID NO 5
<211> LENGTH: 3423
<212> TYPE: DNA
<213> ORGANISM: Corynebacterium glutamicum

<400> SEQUENCE: 5

```
atgtcgactc acacatcttc aacgcttcca gcattcaaaa agatcttggt agcaaaccgc      60
ggcgaaatcg cggtccgtgc tttccgtgca gcactcgaaa ccggtgcagc cacggtagct     120 atttacccc gtgaagatcg gggatcattc caccgctctt tgcttctga agctgtccgc      180 attggtaccg aaggctcacc agtcaaggcg tacctggaca tcgatgaaat tatccggtgca    240 gctaaaaaag ttaaagcaga tgccatttac ccgggatacg gcttcctgtc tgaaaatgcc    300
cagcttgccc gcgagtgtgc ggaaaacggc attactttta ttggcccaac cccagaggtt    360
cttgatctca ccggtgataa gtctcgcgcg gtaaccgccg cgaagaaggc tggtctgcca    420
gttttggcgg aatccacccc gagcaaaaac atcgatgaga tcgttaaaag cgctgaaggc    480
cagacttacc ccatctttgt gaaggcagtt gccggtggtg cggacgcgg tatgcgtttt    540 gttgcttcac ctgatgagct tgcaaatta gcaacagaag catctcgtga agctgaagcg    600
gctttcggcg atggcgcggt atatgtcgaa cgtgctgtga ttaaccctca gcatattgaa    660
gtgcagatcc ttgcgatca cactggagaa gttgtacacc tttatgaacg tgactgctca    720
ctgcagcgtc gtcaccaaaa agttgtcgaa attgcgccag cacagcattt ggatccagaa    780
ctgcgtgatc gcatttgtgc ggatgcagta agttctgcc gctccattgg ttaccagggc    840
gcgggaaccg tggaattctt ggtcgatgaa aagggcaacc acgtcttcat cgaaatgaac    900
ccacgtatcc aggttgagca caccgtgact gaagaagtca ccgaggtgga cctggtgaag    960
gcgcagatgc gcttggctgc tggtgcaacc ttgaaggaat gggtctgac ccaagataag    1020 atcaagaccc acggtgcagc actgcagtgc cgcatcacca cggaagatcc aaacaacggc   1080
ttccgcccag ataccggaac tatcaccgcg taccgctcac caggcggagc tggcgttcgt   1140
cttgacggtg cagctcagct cggtggcgaa atcaccgcac actttgactc catgctggtg   1200
aaaatgacct gccgtggttc cgactttgaa actgctgttg ctcgtgcaca gcgcgcgttg   1260
```

```
gctgagttca ccgtgtctgg tgttgcaacc aacattggtt tcttgcgtgc gttgctgcgg    1320
gaagaggact tcacttccaa gcgcatcgcc accggattca ttgccgatca cccgcacctc    1380
cttcaggctc cacctgctga tgatgagcag ggacgcatcc tggattactt ggcagatgtc    1440
accgtgaaca agcctcatgg tgtgcgtcca aaggatgttg cagctcctat cgataagctg    1500
cctaacatca aggatctgcc actgccacgc ggttcccgtg accgcctgaa gcagcttggc    1560
ccagccgcgt ttgctcgtga tctccgtgag caggacgcac tggcagttac tgataccacc    1620
ttccgcgatg cacaccagtc tttgcttgcg acccgagtcc gctcattcgc actgaagcct    1680
gcggcagagg ccgtcgcaaa gctgactcct gagcttttgt ccgtggaggc ctggggcggc    1740
gcgacctacg atgtggcgat gcgtttcctc tttgaggatc cgtgggacag gctcgacgag    1800
ctgcgcgagg cgatgccgaa tgtaaacatt cagatgctgc ttcgcggccg caacaccgtg    1860
ggatacaccc cgtacccaga ctccgtctgc cgcgcgtttg ttaaggaagc tgccagctcc    1920
ggcgtggaca tcttccgcat cttcgacgcg cttaacgacg tctcccagat gcgtccagca    1980
atcgacgcag tcctggagac caacaccgcg gtagccgagg tggctatggc ttattctggt    2040
gatctctctg atccaaatga aaagctctac accctggatt actacctaaa gatggcagag    2100
gagatcgtca agtctggcgc tcacatcttg gccattaagg atatggctgg tctgcttcgc    2160
ccagctgcgg taaccaagct ggtcaccgca ctgcgccgtg aattcgatct gccagtgcac    2220
gtgcacaccc acgacactgc gggtggccag ctggcaacct actttgctgc agctcaagct    2280
ggtgcagatg ctgttgacgg tgcttccgca ccactgtctg gcaccacctc ccagccatcc    2340
ctgtctgcca ttgttgctgc attgcgcgac acccgtcgcg ataccggttt gagcctcgag    2400
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgcgg atcgtttcga actcatcgaa    2580
gacaactacg cagccgttaa tgagatgctg ggacgcccaa ccaaggtcac ccatcctcc    2640
aaggttgttg gcgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgatccgcc tgccagatgt gcgcacccca    3060
ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg aaggtggcg acttgatcgt cgtcgtttcc    3420
taa                                                                  3423
```

<210> SEQ ID NO 6
<211> LENGTH: 1140
<212> TYPE: PRT
<213> ORGANISM: Corynebacterium glutamicum

<400> SEQUENCE: 6

```
Met Ser Thr His Thr Ser Thr Leu Pro Ala Phe Lys Lys Ile Leu
1               5                   10                  15

Val Ala Asn Arg Gly Glu Ile Ala Val Arg Ala Phe Arg Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
```

```
                       405                 410                 415
        Gln Arg Ala Leu Ala Glu Phe Thr Val Ser Gly Val Ala Thr Asn Ile
                       420                 425                 430

Gly Phe Leu Arg Ala Leu Leu Arg Glu Glu Asp Phe Thr Ser Lys Arg
                       435                 440                 445

Ile Ala Thr Gly Phe Ile Ala Asp His Pro His Leu Leu Gln Ala Pro
                       450                 455                 460

Pro Ala Asp Asp Glu Gln Gly Arg Ile Leu Asp Tyr Leu Ala Asp Val
        465                 470                 475                 480

Thr Val Asn Lys Pro His Gly Val Arg Pro Lys Asp Val Ala Ala Pro
                       485                 490                 495

Ile Asp Lys Leu Pro Asn Ile Lys Asp Leu Pro Leu Pro Arg Gly Ser
                       500                 505                 510

Arg Asp Arg Leu Lys Gln Leu Gly Pro Ala Ala Phe Ala Arg Asp Leu
                       515                 520                 525

Arg Glu Gln Asp Ala Leu Ala Val Thr Asp Thr Thr Phe Arg Asp Ala
                       530                 535                 540

His Gln Ser Leu Leu Ala Thr Arg Val Arg Ser Phe Ala Leu Lys Pro
        545                 550                 555                 560

Ala Ala Glu Ala Val Ala Lys Leu Thr Pro Glu Leu Leu Ser Val Glu
                       565                 570                 575

Ala Trp Gly Gly Ala Thr Tyr Asp Val Ala Met Arg Phe Leu Phe Glu
                       580                 585                 590

Asp Pro Trp Asp Arg Leu Asp Glu Leu Arg Glu Ala Met Pro Asn Val
                       595                 600                 605

Asn Ile Gln Met Leu Leu Arg Gly Arg Asn Thr Val Gly Tyr Thr Pro
                       610                 615                 620

Tyr Pro Asp Ser Val Cys Arg Ala Phe Val Lys Glu Ala Ala Ser Ser
        625                 630                 635                 640

Gly Val Asp Ile Phe Arg Ile Phe Asp Ala Leu Asn Asp Val Ser Gln
                       645                 650                 655

Met Arg Pro Ala Ile Asp Ala Val Leu Glu Thr Asn Thr Ala Val Ala
                       660                 665                 670

Glu Val Ala Met Ala Tyr Ser Gly Asp Leu Ser Asp Pro Asn Glu Lys
                       675                 680                 685

Leu Tyr Thr Leu Asp Tyr Tyr Leu Lys Met Ala Glu Glu Ile Val Lys
                       690                 695                 700

Ser Gly Ala His Ile Leu Ala Ile Lys Asp Met Ala Gly Leu Leu Arg
        705                 710                 715                 720

Pro Ala Ala Val Thr Lys Leu Val Thr Ala Leu Arg Arg Glu Phe Asp
                       725                 730                 735

Leu Pro Val His Val His Thr His Asp Thr Ala Gly Gly Gln Leu Ala
                       740                 745                 750

Thr Tyr Phe Ala Ala Ala Gln Ala Gly Ala Asp Ala Val Asp Gly Ala
                       755                 760                 765

Ser Ala Pro Leu Ser Gly Thr Thr Ser Gln Pro Ser Leu Ser Ala Ile
                       770                 775                 780

Val Ala Ala Phe Ala His Thr Arg Arg Asp Thr Gly Leu Ser Leu Glu
        785                 790                 795                 800

Ala Val Ser Asp Leu Glu Pro Tyr Trp Glu Ala Val Arg Gly Leu Tyr
                       805                 810                 815

Leu Pro Phe Glu Ser Gly Thr Pro Gly Pro Thr Gly Arg Val Tyr Arg
                       820                 825                 830
```

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Leu Gly Asn Pro Pro Gly Gly Trp
        915                 920                 925

Pro Glu Pro Leu Arg Thr Arg Ala Leu Glu Gly Arg Ser Glu Gly Lys
        930                 935                 940

Ala Pro Leu Thr Glu Val Pro Glu Gly Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 7
<211> LENGTH: 3423
<212> TYPE: DNA
<213> ORGANISM: Corynebacterium glutamicum

<400> SEQUENCE: 7
atgtcgactc acacatcttc aacgcttcca gcattcaaaa agatcttggt agcaaaccgc     60
ggcgaaatcg cggtccgtgc tttccgtgca gcactcgaaa ccggtgcagc cacggtagct    120
atttaccccc gtgaagatcg gggatcattc caccgctctt ttgcttctga agctgtccgc    180
attggtaccg aaggctcacc agtcaaggcg tacctggaca tcgatgaaat tatcggtgca    240
gctaaaaaag ttaaagcaga tgccatttac ccgggatacg gcttcctgtc tgaaaatgcc    300

-continued

| | |
|---|---|
| cagcttgccc gcgagtgtgc ggaaaacggc attactttta ttggcccaac cccagaggtt | 360 |
| cttgatctca ccggtgataa gtctcgcgcg gtaaccgccg cgaagaaggc tggtctgcca | 420 |
| gttttggcgg aatccacccc gagcaaaaac atcgatgaga tcgttaaaag cgctgaaggc | 480 |
| cagacttacc ccatctttgt gaaggcagtt gccggtggtg gcggacgcgg tatgcgtttt | 540 |
| gttgcttcac ctgatgagct tcgcaaatta gcaacagaag catctcgtga agctgaagcg | 600 |
| gctttcggcg atggcgcggt atatgtcgaa cgtgctgtga ttaaccctca gcatattgaa | 660 |
| gtgcagatcc ttggcgatca cactggagaa gttgtacacc tttatgaacg tgactgctca | 720 |
| ctgcagcgtc gtcaccaaaa agttgtcgaa attgcgccag cacagcattt ggatccagaa | 780 |
| ctgcgtgatc gcatttgtgc ggatgcagta aagttctgcc gctccattgg ttaccagggc | 840 |
| gcggaaccg tggaattctt ggtcgatgaa aagggcaacc acgtcttcat cgaaatgaac | 900 |
| ccacgtatcc aggttgagca caccgtgact gaagaagtca ccgaggtgga cctggtgaag | 960 |
| gcgcagatgc gcttggctgc tggtgcaacc ttgaaggaat tgggtctgac ccaagataag | 1020 |
| atcaaggccc acggggcagc actgcagtgc cgcatcacca cggaagatcc aaacaacggc | 1080 |
| ttccgcccag ataccggaac tatcaccgcg taccgctcac caggcggagc tggcgttcgt | 1140 |
| cttgacggtg cagctcagct cggtggcgaa atcaccgcac actttgactc catgctggtg | 1200 |
| aaaatgacct gccgtggttc cgactttgaa actgctgttg ctcgtgcaca gcgcgcgttg | 1260 |
| gctgagttca ccgtgtctgg tgttgcaacc aacattggtt tcttgcgtgc gttgctgcgg | 1320 |
| gaagaggact tcacttccaa gcgcatcgcc accggattca ttgccgatca cccgcacctc | 1380 |
| cttcaggctc cacctgctga tgatgagcag ggacgcatcc tggattactt ggcagatgtc | 1440 |
| accgtgaaca agcctcatgg tgtgcgtcca aaggatgttg cagctcctat cgataagctg | 1500 |
| cctaacatca aggatctgcc actgccacgc ggttcccgtg accgcctgaa gcagcttggc | 1560 |
| ccagccgcgt ttgctcgtga tctccgtgag caggacgcac tggcagttac tgataccacc | 1620 |
| ttccgcgatg cacaccagtc tttgcttgcg acccgagtcc gctcattcgc actgaagcct | 1680 |
| gcggcagagg ccgtcgcaaa gctgactcct gagcttttgt ccgtggaggc ctggggcggc | 1740 |
| gcgacctacg atgtggcgat gcgtttcctc tttgaggatc cgtgggacag gctcgacgag | 1800 |
| ctgcgcgagg cgatgccgaa tgtaaacatt cagatgctgc ttcgcggccg caacaccgtg | 1860 |
| ggatacaccc cgtacccaga ctccgtctgc cgcgcgtttg ttaaggaagc tgccagctcc | 1920 |
| ggcgtggaca tcttccgcat cttcgacgcg cttaacgacg tctcccagat gcgtccagca | 1980 |
| atcgacgcag tcctggagac caacaccgcg gtagccgagg tggctatggc ttattctggt | 2040 |
| gatctctctg atccaaatga aaagctctac accctggatt actacctaaa gatggcagag | 2100 |
| gagatcgtca agtctggcgc tcacatcttg gccattaagg atatggctgg tctgcttcgc | 2160 |
| ccagctgcgg taaccaagct ggtcaccgca ctgcgccgtg aattcgatct gccagtgcac | 2220 |
| gtgcacaccc acgacactgc gggtggccag ctggcaacct actttgctgc agctcaagct | 2280 |
| ggtgcagatg ctgttgacgg tgcttccgca ccactgtctg gcaccacctc ccagccatcc | 2340 |
| ctgtctgcca ttgttgctgc attgcgcgca cccgtcgcg ataccggttt gagcctcgag | 2400 |
| gctgtttctg acctcgagcc gtactgggaa gcagtgcgcg gactgtacct gccatttgag | 2460 |
| tctggaaccc caggcccaac cggtcgcgtc taccgccacg aaatcccagg cggacagttg | 2520 |
| tccaacctgc gtgcacaggc caccgcactg ggccttgcgg atcgtttcga actcatcgaa | 2580 |
| gacaactacg cagccgttaa tgagatgctg ggacgcccaa ccaaggtcac ccatcctcc | 2640 |
| aaggttgttg gcgacctcgc actccacctc gttggtgcgg gtgtggatcc agcagacttt | 2700 |

```
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgatccgcc tgccagatgt gcgcaccca    3060 ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg aaggtggcg acttgatcgt cgtcgtttcc    3420
taa                                                                  3423

<210> SEQ ID NO 8
<211> LENGTH: 3423
<212> TYPE: DNA
<213> ORGANISM: Corynebacterium glutamicum

<400> SEQUENCE: 8
atgtcgactc acacatcttc aacgcttcca gcattcaaaa agatcttggt agcaaaccgc      60
ggcgaaatcg cggtccgtgc tttccgtgca gcactcgaaa ccggtgcagc cacggtagct     120
atttaccccc gtgaagatcg gggatcattc caccgctctt tgcttctga agctgtccgc     180 attggtaccg aaggctcacc agtcaaggcg tacctggaca tcgatgaaat tatcggtgca     240
gctaaaaaag ttaaagcaga tgccatttac ccgggatacg gcttcctgtc tgaaaatgcc     300
cagcttgccc gcgagtgtgc ggaaaacggc attactttta ttggcccaac cccagaggtt     360
cttgatctca ccggtgataa gtctcgcgcg gtaaccgccg cgaagaaggc tggtctgcca     420
gttttggcgg aatccacccc gagcaaaaac atcgatgaga tcgttaaaag cgctgaaggc     480
cagacttacc ccatctttgt gaaggcagtt gccggtggtg gcggacgcgg tatgcgtttt     540
gttgcttcac ctgatgagct tcgcaaatta gcaacagaag catctcgtga agctgaagcg     600
gctttcggcg atggcgcggt atatgtcgaa cgtgctgtga ttaaccctca gcatattgaa     660
gtgcagatcc ttggcgatca cactggagaa gttgtacacc tttatgaacg tgactgctca     720
ctgcagcgtc gtcaccaaaa agttgtcgaa attgcgccag cacagcattt ggatccagaa     780
ctgcgtgatc gcatttgtgc ggatgcagta aagttctgcc gctccattgg ttaccagggc     840
gcgggaaccg tggaattctt ggtcgatgaa aagggcaacc acgtcttcat cgaaatgaac     900
ccacgtatcc aggttgagca caccgtgact gaagaagtca ccgaggtgga cctggtgaag     960
gcgcagatgc gcttggctgc tggtgcaacc ttgaaggaat tgggtctgac ccaagataag    1020
atcaaggccc acgggcagc actgcagtgc cgcatcacca cggaagatcc aaacaacggc    1080
ttccgcccag ataccggaac tatcaccgcg taccgctcac caggcggagc tggcgttcgt    1140
cttgacggtg cagctcagct cggtggcgaa atcaccgcac actttgactc catgctggtg    1200
aaaatgacct gccgtggttc cgactttgaa actgctgttg ctcgtgcaca gcgcgcgttg    1260
gctgagttca ccgtgtctgg tgttgcaacc aacattggtt tcttgcgtgc gttgctgcgg    1320
```

-continued

```
gaagaggact tcacttccaa gcgcatcgcc accggattca ttgccgatca cccgcacctc    1380
cttcaggctc cacctgctga tgatgagcag ggacgcatcc tggattactt ggcagatgtc    1440
accgtgaaca agcctcatgg tgtgcgtcca aaggatgttg cagctcctat cgataagctg    1500
cctaacatca aggatctgcc actgccacgc ggttcccgtg accgcctgaa gcagcttggc    1560
ccagccgcgt ttgctcgtga tctccgtgag caggacgcac tggcagttac tgataccacc    1620
ttccgcgatg cacaccagtc tttgcttgcg acccgagtcc gctcattcgc actgaagcct    1680
gcggcagagg ccgtcgcaaa gctgactcct gagcttttgt ccgtggaggc ctggggcggc    1740
gcgacctacg atgtggcgat gcgtttcctc tttgaggatc cgtgggacag gctcgacgag    1800
ctgcgcgagg cgatgccgaa tgtaaacatt cagatgctgc ttcgcggccg caacaccgtg    1860
ggatacaccc cgtacccaga ctccgtctgc cgcgcgtttg ttaaggaagc tgccagctcc    1920
ggcgtggaca tcttccgcat cttcgacgcg cttaacgacg tctcccagat gcgtccagca    1980
atcgacgcag tcctggagac caacaccgcg gtagccgagg tggctatggc ttattctggt    2040
gatctctctg atccaaatga aaagctctac accctggatt actacctaaa gatggcagag    2100
gagatcgtca agtctggcgc tcacatcttg gccattaagg atatggctgg tctgcttcgc    2160
ccagctgcgg taaccaagct ggtcaccgca ctgcgccgtg aattcgatct gccagtgcac    2220
gtgcacaccc acgacactgc gggtggccag ctggcaacct actttgctgc agctcaagct    2280
ggtgcagatg ctgttgacgg tgcttccgca ccactgtctg gcaccacctc ccagccatcc    2340
ctgtctgcca ttgttgctgc attgcgcgcac accgtcgcg ataccggttt gagcctcgag    2400
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgcgg atcgtttcga actcatcgaa    2580
gacaactacg cagccgttaa tgagatgctg ggacgcccaa ccaaggtcac cccatcctcc    2640
aaggttgttg gcgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgagccggc tgccagatgt gcgcacccca    3060
ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg gaaggtggcg acttgatcgt cgtcgtttcc    3420
taa                                                                  3423
```